(12) United States Patent
Whittaker

(10) Patent No.: US 12,569,808 B2
(45) Date of Patent: Mar. 10, 2026

(54) CARBON CAPTURE BY ALGAL INOCULATION OF OCEAN ICE AND/OR SEA ICE

(71) Applicant: John Whittaker, Caernarfon (GB)

(72) Inventor: John Whittaker, Caernarfon (GB)

( * ) Notice: Subject to any disclaimer, the term of this patent is extended or adjusted under 35 U.S.C. 154(b) by 143 days.

(21) Appl. No.: 18/376,832

(22) Filed: Oct. 4, 2023

(65) Prior Publication Data

US 2024/0109033 A1 Apr. 4, 2024

Related U.S. Application Data

(60) Provisional application No. 63/413,046, filed on Oct. 4, 2022.

(51) Int. Cl.
| | |
|---|---|
| *C12N 1/12* | (2006.01) |
| *B01D 53/85* | (2006.01) |
| *B05B 15/60* | (2018.01) |

(52) U.S. Cl.
CPC .............. *B01D 53/85* (2013.01); *B05B 15/60* (2018.02); *C12N 1/12* (2013.01); *B01D 2251/95* (2013.01); *B01D 2257/504* (2013.01)

(58) Field of Classification Search
CPC ....................................................... C12N 1/12
See application file for complete search history.

(56) References Cited

PUBLICATIONS

Zheng et al., "Low-temperature adaptation of the snow alga *Chlamydomonas nivalis* is associated with the photosynthetic system regulatory process," Frontiers in Microbiology 11(1233):1-15, 2020.*

* cited by examiner

*Primary Examiner* — Rosanne Kosson

(57) ABSTRACT

The invention features a low cost nature-based carbon sequestering vaccine presenting capacity to restore global Carbon Dioxide to pre-industrial levels over a short, perhaps singly decade use across multiple deployments. This low tech, low cost, high impact, 100% nature based solution is carbon negative during its production and throughout deployment using multiple embodiments that capture and sequestrate carbon dioxide from at least a kiloton approaching a gigaton or beyond scale. The invention uses already developed technologies and biological methods in producing a "vaccine" for inoculating selected unpopulated or sparsely populated geozones with low potentials for disrupting human activities. Embodiments feature deployment of the vaccine into extreme cold environments with minor or non-existent negative externalities. Extremophilic algal cohorts are selectively adapted by growth in serial culture for spreading at sites where the algae growth turns carbon dioxide from the ambient air into biomass that sequesters the carbon for centuries.

19 Claims, No Drawings

CARBON CAPTURE BY ALGAL INOCULATION OF OCEAN ICE AND/OR SEA ICE

The present invention relates to climate change and provides mitigation methods with capacities to capture giga-tons of carbon dioxide ($CO_2$) through its efficient, low tech and low-cost deployment. Widespread deployment not only has the potential to create a carbon neutral environment at manufacture sites and through widespread deployment could eventually reverse climate change to pre-industrial levels potentially within a decade. This invention is carbon negative in both production and deployment. i.e., it entirely offsets energy costs of production, transportation, and deployment. The product itself does not produce any net $CO_2$ emissions and its whole purpose is to capture $CO_2$ from the atmosphere.

The products and methods of this invention fix carbon (as present in $CO_2$) from the atmosphere directly in situ utilizing low cost technologies and low cost energy conversion from ambient light energy to carbon sequestering chemical energy. By administering the invention product formed as a Climate Vaccine, extreme weather events associated with industrial heat absorbing gases can be reduced. The invention features incorporating selectively cultured psychrophilic microalgal species onto ice sheet surfaces or into the troposphere to remove high volumes of $CO_2$ directly from the atmosphere and thereby to reduce or reverse the recent rise in global temperatures associated with human industrial activities. Like any inoculation, it is important that the species, dose, timing, and location are pre-determined for optimal planning and efficacy.

BACKGROUND

Carbon dioxide ($CO_2$) is a greenhouse gas that is a major contributor to the increase in global temperature. It is proposed by the inventor that by administering psychrophilic microalgal species onto breakaway floating ice sheets and icebergs that the resulting cell growth on such surfaces will remove the high amounts of $CO_2$ directly from the atmosphere. This activity will reduce or even reverse the rise in global temperature to return closer to pre-industrial levels. Icebergs and are naturally occurring uninhabitable temporary floating structures which appear and disappear seasonally or cyclically. Floating ice sheets are distributed naturally by ocean currents and as such are ideal sites for utilizing the opportunity for carbon capture and deposition into the ocean biomass. The sea ice sheets are formed from fresh water rather than salt water, which is essential for the vaccine. It is proposed that by administering the vaccine onto breakaway floating ice sheets and icebergs that the resulting cell growth will remove the high levels of carbon dioxide directly from the atmosphere. This application permits $CO_2$ capture rates on a kiloton to megaton scale. The invention is also compatible for less motile, e.g., frozen lake surface, man made ice field or ice rink, snowcap, glacier, frozen canal or river, etc.

A main problem facing large scale carbon capture is the land requirement and the opportunity cost of re-purposing the land mass. Costs in terms of technology and energy are tremendous. This present invention fixes carbon from the atmosphere directly within the atmosphere utilizing low cost technology and low cost energy conversion avoiding the problematic re-purposing of land.

The Vaccine

Production of the vaccine itself captures $CO_2$ on a kiloton scale

A first embodiment for manufacturing the Climate Vaccine features photobioreactors that are placed in industrial or other facilities that emit large amounts (higher than ambient concentrations) of $CO_2$. This embodiment in its simplest application converts industrial sourced $CO_2$ to solid biomass thus preventing atmospheric contamination. A second embodiment piggybacking on this, involves harvesting, packaging, and then deploying the biomass product in environments such as: ice rink units that are functionally constructed for direct capture of $CO_2$ from surrounding air, natural ice fields, including icebergs or ice sheets, atmospheric clouds, etc. The biomass invention is a product of Rubisco which has applied to it the name Climate Vaccine® aka: Rubisco Climate Vaccine®.

Post manufacture, versions of the Climate Vaccine may be deployed across a variety of environments, e.g., in the cloud layer of the troposphere and/or on existing natural ice sheets such as icebergs and ice sheets. The equation for Photosynthesis $6CO_2+6H_2O{\rightarrow}C_6H_{12}O_6+6O_2$. Practicing the instant invention stimulates massive amounts of photosynthetic algal metabolism and growth. The result is disappearance of $CO_2$ from the ambient atmosphere with increased release of $O_2$. Both these effects serve to counter the deleterious effects of the industrial age appearing in our atmosphere.

The RubisCO Climate Vaccine® (RCV) comprises a cultured cocktail of specifically optimized extremophile psychrophile micro-organisms, optimally together with a blend of constituent accelerants. The accelerants are selectable by the practitioner according to desired criteria, e.g., cost, volume, mass, mass:volume ratio, color, packaging, storage, regulation, etc. The cultured cocktail may comprise a single seed species or strain adapted to rapid growth and proliferation under culturing conditions approximating or mimicking conditions to be encountered in the select environment after local Vaccine deployment. For wider (non-specific) applications a cocktail not specific to a particular deployment zone may comprise two or more cultured species. The packaged plurality of species may be desired for general deployments when the optimal species or strain has not been addressed. The accelerants may be optimally designed with the cultured cocktail for inoculation at specific locations to capture carbon dioxide directly from the atmosphere.

The RubisCO Climate Vaccine® (RCV) comprises a cultured cocktail of specifically optimized extremophile psychrophile micro-organisms optimally together with a blend of constituent accelerants. The accelerants are optimally designed with the cultured cocktail for inoculation at specific locations to capture carbon dioxide directly from the atmosphere.

Post deployment, the vaccine is self-propagating as it consumes and removes $CO_2$ from its industrial or other facility or rink or ice field in the existing or natural environment. The Vaccine live elements absorb sunlight and $CO_2$ as they grow and proliferate forming progeny live elements that grow and proliferate. Pre-deployment, RSV can be readily stored in small 100 to 1,000 ml bottles or larger, jugs, barrels, tank, sized containers in ambient conditions, e.g., a ventilated warehouse, without any special requirements. Aqueous cultures may be further processed by lyophilization or freeze drying for compact long term storage and as an alternative to liquid prep-spraying at deployment. The reduced weight and volume of the lighter powdered format inoculant can result in lower cost deployment, larger inoculation area from a single inoculation run, increased dispersion, lessened logistical problems and a larger potential direct capture of gaseous $CO_2$ from the atmosphere.

In preferred embodiments, during RSV production, specifically site adapted portable Carbon Dioxide Removal (CDR) units at industrial sites that are producing significant $CO_2$ emissions to avoid atmospheric release of the site's $CO_2$. The CDR units are optionally further enabled by running commercially purchased photobioreactors in which regulated $CO_2$ will boost the growth and replication of the process. Commercially available units have remote sensing, analytical and data monitoring built in. They require minimum manual intervention, e.g., on a multi-day, weekly, bi-weekly basis. Commercial availability enables rapid uptake of this invention for general widespread use. Preferred units are the same size as the 20 ft shipping containers and therefore are easy to ship and deploy by common transport means and require minimal on-site set-up and very little space. Such units can be sited externally (outside an existing wall) or within a production facility that is producing $CO_2$. Flue gas or exhaust air is drawn into extraction units where carbon will be removed from the $CO_2$ intake into the bio-processor and resultant oxygen released into the atmosphere. Many industries produce large quantities of $CO_2$ during their processes including, but not limited to: steel, plastic, fertilizer manufacturers, brewers, bakers, yeast providers, and distilleries.

The food or distillation processes, e.g., for alcohol or breads, first involve fermentation by yeasts that consume carbohydrate food sources to form alcohol. A major by-product from the metabolism is $CO_2$. A dedicated bioreactor fed with the fermentation emissions will capture the emitted $CO_2$ reducing the beverage's or bread's carbon footprint. But a secondary benefit arises from using the feed to grow the RC Vaccine These portable "$CO_2$ Removal Units" though reducing the carbon footprint of the associated plant, are thus primarily used to produce Rubisco Climate Vaccine® or analogous product. However, as previously mentioned, during vaccine production, they also operate as carbon removal facilities. This capture during the vaccine production phase, while significant, is on a smaller gross scale than achievable after vaccine deployment. Additionally, the units could be designed to produce by-products like, e.g., skin care and animal food additives during vaccine element propagation. CDR units can also operate under ambient conditions (capture atmospheric air). However higher levels of $CO_2$ are preferred to boost the CDR output performance, to possibly produce carbon credits, and to lower costs.

Applications.

The RCV is readily transported to the deployment site(s) in a concentrated form. Prior to or at the deployment site(s) the concentrated RCV is diluted with water to the required dilution. Dilution rates are influenced by several factors; however, the ratio is in the order of 8 parts per 1000, i.e., 8 ml of a concentrate, e.g., 20,000 to 750,000 cells/ml, per litre, is one exemplary step in distribution/deployment. Depending on deployment zone and accessibility, the practitioner. For example may wish to transport smaller or larger masses and volumes of the vaccine concentrate for higher or lower fold dilution at the end site. Serial dilution may be practiced. Concentrates therefore may start or arrive at desired concentrations at different deployment stages, e.g., about 50,000, 60,000, 75,000, 100,000, 150,000, 250,000, 400,000, 500,000, 750,000 cells/ml. Therefore it is easy and economical to transport the vaccine to different sites for deployment. A freeze dried algal culture formed as a fine powder, e.g., pellet average mass ~1-10×10$^{-4}$ g, permits simple deployment over a large area with significant gravitational draw for propulsion to its target proliferation site. The reduced payload weight and volume of the light powdered format inoculant onto floating sea ice or other surfaces will result in lower cost deployment, larger inoculation area, increased dispersion, lessened logistical problems and a larger potential direct capture of gaseous $CO_2$ from the atmosphere especially considering the logistics involved in deployment at extreme latitudes.

Typical base cultures prior to dilution at dispersal site or for dilution prior to transport to the dispersal site may be maintained in a relatively concentrated stock, e.g., about 15,000 to 100,000 cells/ml. Cell numbers will depend on the practitioners plans, perhaps dependent on the route of dilution, size of cell, viscosity of medium, size of containers for culture and diluent, output of the CDR, etc. While typical dilutions are in the order of 10$^2$, the precise dilution ratio is at the practitioners discretion. For example, a greater dilution may be used when higher volume/area ratios are required by the machinery. Final concentrations for easy delivery to the targeted zones may typically range from about 150,000 cells per liter or several fold higher cell concentrations, e.g., 500,000 to 750,000 cells per liter. Precise cell counts are not required for successful deployment. Ease of dilution and dispensing, volume or mass capacity of the delivery vehicle, fineness of the spray, available container sizes, etc., are several of the considerations a practitioner may consider in the stock and final concentrations. Thus a practitioner may at their discretion select a targeted concentration, e.g., about 1.75×10$^5$, 2×10$^5$, 3×10$^5$, 4×10$^5$, 4.5×10$^5$, 5×10$^5$, 6×10$^5$, 7×10$^5$, 8×10$^5$, 9×10$^5$, 10$^6$, etc., dependent on equipment and factors at hand.

The locations for application, the amount and its developmental status for each inoculation is governed by threshold values and predicted levels of temperature, atmospheric pressure, altitudes, humidity, latitude, diurnal light period and intensity, that will enable optimized growth and replication efficacy until eventual deposition in melt water. Optimization, selecting culture conditions for the intended deployment(s), is preferred for maximal $CO_2$ capture, but non-optimized cultures will still remove significant carbon from the air. Using wild type algal strains harvested from zones at or similar to a specific deployment zone can facilitate the adaptation processes. The RCV is expected to adapt to greater capture efficiencies as it continues to proliferate at the deployment site.

Melting glaciers naturally run off algae into the oceans. The melting inoculated icebergs that also naturally supply nutrients to the ocean also serve to slowly deposit and distribute the algae into the ocean as a natural microscopic food source into food chains where organisms will incorporate the RCV progeny into their bodies with eventual deposits to the deep ocean sea floor—where the carbon may remain locked for millions of years. Diluted Vaccine is disbursed directly onto the ice sheet e.g., from a plane or drone in the same way as crop dusting or from a land vehicle, e.g., tracked or towed vehicle. Preliminary data and estimates show that inoculating an ice sheet of 1000 km$^2$ can capture in excess of 5 megatons of $CO_2$ over a period of 36 days in optimal Spring conditions.

Sea or Ocean Ice is already carrying sea ice algae and snow algae into the oceans naturally on a small scale. The present invention turbocharger this process massively and directly captures $CO_2$ from the atmosphere and sequesters the resulting carbon into ocean food chains and detritus at ocean depths for millions of years.

Snow or glacial algae are found on all continents, and most species are in the Chlamydomonadales (Chlorophyta) and Zygnematales (Streptophyta). Other algal groups include euglenoids, cryptomonads, chrysophytes, dinoflagellates, and cyanobacteria. They can live under extreme conditions of temperatures near 0° C., high irradiance levels in open exposures, low irradiance levels under tree canopies or deep in snow, acidic pH, low conductivity, and desiccation after snow melt. These primary producers may color snow green, golden-brown, red, pink, orange, or purple-grey, and they are part of communities that include other eukaryotes, bacteria, archaea, viruses, and fungi. They are an important component of the global biosphere and carbon and water cycles. Life cycles in the *Chlamydomonas-chloromonas-Chlainomonas* complex include migration of flagellates in liquid water and formation of resistant cysts. Selected strains of these algae have potential for producing food or fuel products. Organisms regarded as true snow and glacial algae thrive in a liquid water film between melting snow and ice crystals, and usually do not propagate outside of this habitat. Serial culturing to formulate the vaccine should select for growth at liquid-gas interface.

Snow and glacial algae are examples of how life can adapt to harsh environmental conditions in terms of solar irradiance, low temperatures or nutrients, and show that photo-troph extremophiles perform well in putative extreme habitats such as melting snowpacks or glacial surfaces. As a result, these microbes have been considered as Earth analogs for life outside our planet (Havig and Hamilton 2019, Vimercati et al. 2019b). When there is liquid water, the algae can reproduce and bloom within days or weeks. During this time, they can start green, then turn red, or stay green or stay red—it depends on the algal species. Such microorganisms have adapted (evolved) to survive under a wide variety of conditions. As all living organisms, when they grow, they metabolize nutrients to form their biomolecular structures. For photosynthetic organisms an important nutrient is $CO_2$.

Glacier algae photosynthesize at surprisingly high rates considering their thermodynamically unfavorable cold environment (Remias et al., 2009, 2012a; Cook et al., 2012; Yallop et al., 2012; Williamson et al., 2018). Recent estimates of glacier algal net productivity in southwestern Greenland ranged from ˜0.5 to 1 mg C $l^{-1}$ $d^{-1}$, based on ice containing dense algal communities (˜104 cells $ml^{-1}$; Yallop et al., 2012; Williamson et al., 2018). While few attempts have been made to constrain the importance of glacier algae for supraglacial carbon budgets, recent modeling efforts for regions of the southwestern GrIS have highlighted the major contribution that blooms can make to supraglacial carbon fixation (Cook et al., 2012; Williamson et al., 2018), with an average net carbon fixation of ˜16±8 kg C $km^2$ estimated for the 2016 ablation season (Williamson et al., 2018). This can lead to accumulation of autochthonous organic carbon within glacier algal-rich habitats (Musilova et al., 2017). Labile organic carbon not consumed in situ by secondary production may be exported via meltwater flushing for utilization within downstream subglacial and periglacial ecosystems (Musilova et al., 2017; Smith et al., 2017).

Blooms of algae on glacier and ice sheet surfaces have been reported from across the cryosphere, including Antarctica (Ling and Seppelt, 1993), Alaska (Takeuchi, 2001, 2013; Ganey et al., 2017), Siberia (Takeuchi et al., 2006, 2015; Tanaka et al., 2016), the Himalayas (Yoshimura et al., 1997), Svalbard (Remias et al., 2012a), and Greenland (Uetake et al., 2010; Yallop et al., 2012; Stibal et al., 2017; Williamson et al., 2018), indicating their apparent ubiquity in supraglacial systems. Blooms initiate following snow line retreat, with algal biomass observed to increase in surface ice through time (Stibal et al., 2017; Williamson et al., 2018). In contrast to snow algae (Hoham and Duval, 2001), the absence of a flagellated life stage prevents active motility of glacier algae, and thus, colonization of new ice environments during bloom events is likely dependent on local hydrological or aeolian forcing (Kristiansen, 1996). On the Greenland Ice Sheet (GrIS), population doubling times have been estimated at 3.75-5.5 days (Stibal et al., 2017; Williamson et al., 2018), with cell densities observed to range from 9.1×104 to 29.5×104 cells ml-1 at marginal locations (Yallop et al., 2012), from <100 to 8.5×$10^4$ cells $ml^{-1}$ ˜30 km into the south-westerly region of the ice sheet (Stibal et al., 2017), and from 1.6×104 cells ml-1 to 0 cells ml-1 from ˜30 km inland to the snow line (Williamson et al., 2018). The influences on spatial patterning in biomass are multifaceted. Observations of algal biomass on mountain glaciers (e.g., Yoshimura et al 1997; Takeuchi and Kohshima, 2004; Takeuchi et al., 2009) show declines in biomass with increasing altitude, while observations from the GrIS's "dark zone" (a conspicuous area of dark ice that appears across the west and southwestern sectors of the ice sheet each summer; Wientjes and Oerlemans, 2010) show a decrease in biomass away from the ice sheet margin (Williamson et al., 2018). Considered jointly, these intimate that longer melt seasons support algal biomass development through promoting solar radiation input, nutrient availability, and diminished snow cover (Yoshimura et al., 1997). Decreases in biomass can be driven by rainfall-associated flushing events (Stibal et al., 2017), and biomass is potentially restricted close to the terminus of glaciers by mineral dust covering that can limit photosynthesis and/or by increased meltwater flushing on steeper slopes (Takeuchi, 2013). Interspeccial interactions also influence the relative dominance of glacier algae at the glacier scale, with specialists dominating more stable ice environments and generalist species becoming dominant in areas characterized by less stable conditions, e.g., frequent changing between snow and ice environments (Yoshimura et al., 1997).

It has been shown in situ in that snow algae have the capability of capture of 257 tonnes of carbon $Km^{-2}$ $year^{-1}$ (Andrew Gray, et al, 2021).

The naturally occurring wild type of the microorganism species used as source material for the vaccine, flourish and capture carbon dioxide in large amounts where they grow. This invention culturally modifies wild type organisms for optimal activity at the target site where Climate Vaccine is administered as a growth optimized cocktail directly at the site in quantities for accelerated carbon capture.

The Climate Vaccine is superior to other Carbon Capture alternatives, yet is proposed for use in conjunction with many similarly purposed activities. A visually striking adaptation of glacier algae to their environment is the production of a specialist pigment absorbing ultraviolet and visible light (purpurogallin carboxylic acid-6-O-Beta-D-glucopyranoside), contained within lipid bodies and vacuoles occupying a large proportion of the cell; Remias et al., 2009, 2012a, b). In addition to the suite of light-harvesting and photoprotective pigments typical of green microalgae (Remias et al., 2009, 2012b; Williamson et al., 2018), this phenolic pigment is primarily assumed to serve a photoprotective role, shading the underlying chloroplasts from the significant PAR and UV regime apparent in supraglacial systems (Remias et al., 2009, 2012b; Williamson et al., 2018). It also likely serves to convert the abundant light energy to heat, allowing melt water generation local to the cell (Dial et al., 2018). To date, the capacity of glacier algal phenols to provide photoprotection has been indirectly evidenced by a lack of saturation during photosynthesis-irradiance curves (Remias et al., 2012a, b) and fluorescence-based rapid light curves (Yallop et al., 2012), ranging up to 2000 $\mu$mol photons m$^2$/s. Given that the photosynthetic machinery is adversely affected by several cold associated stressors (i.e., freezing and desiccation reduce cell membrane fluidity impacting electron transport; low temperatures mimic high-light stress by decreasing the efficiency of metabolic electron sinks; Lyon and Mock, 2014), it is likely that glacier algae purpurogallins serve to protect the cell against multiple stressors. Little further information on specific glacier algae adaptations to life in surface ice is available, with this knowledge gap strongly exacerbated by their reluctance to be cultured under laboratory conditions (Remias et al., 2009, 2012a). Though conjugation in *A. nordenskiöldii* field populations has been observed in Svalbard (Remias et al., 2012a, b) and the GrIS (C. Williamson, personal observation), the production of a dormant zygospore does not appear to be an overwintering strategy, with glacier algae observed to overwinter in a non-cyst-like, vegetative state (Remias et al., 2009). This likely permits rapid resumption of physiological activity on initiation of the relatively short summer growth season. Glacier algae also demonstrate increased concentrations of sugars and polyols (i.e., compatible solutes) (Roser et al., 1992; Chapman et al., 1994), consistent with known cold tolerance mechanisms in other psychrophilic microalgae (Welsh, 2006; Casanueva et al., 2010; Lyon and Mock, 2014). However, knowledge on other features typically associated with cold tolerance in microalgae, e.g., membrane fluidity, production of specialist enzymes, "cold-shock" proteins or extracellular polymeric substances, is currently lacking.

Recent research led by scientists from the University of Bristol reveals that the microscopic algae thriving along the edge of the Greenland Ice Sheet cause widespread darkening. This darkening is important as darker ice absorbs more sunlight energy and melts faster, accelerating the overall melting of the ice, which is the single largest contributor to global sea level rises. Extremophile microscopic algae, or so-called 'glacier algae', can live in the upper few centimeters of ice on the surfaces of glaciers and ice sheets and can form widespread blooms during the summer melt season. Researchers from Aarhus University have measured a new world record: small ice algae on the underside of the Arctic Sea ice live and grow at a light level corresponding to only 0.02 percent of the light at the surface of the ice. Algae are the primary component of the Arctic food web and produce food far earlier in the year than previously thought.

This is the lowest light level where active photosynthesis and growth of ice algae have been observed. Kasper Hancke et al, Extreme Low Light Requirement for Algae Growth Underneath Sea Ice: A Case Study from Station Nord, NE Greenland, Journal of Geophysical Research: Oceans (2018). DOI: 10.1002/2017JC013263C013263.

Phosphorus, a mineral found in dust, is a key nutrient for an extensive glacier algae bloom on Greenland's ice sheet, known as the "dark zone." As the algae grow, the ice becomes darker, decreasing its ability to reflect sunlight and causing the ice to melt (JMcCutcheon et al 2021) (www-.nature.com/articles/s41467-020-20627-w).

Effect of Iron

The Redfield Ratio

The Redfield ratio describes the relative atomic concentrations of critical nutrients in plankton biomass and is conventionally written "106 C:16 N:1 P." This expresses the fact that one atom of phosphorus and 16 of nitrogen are required to "fix" 106 carbon atoms (or 106 molecules of $CO_2$). Research expanded this constant to "106 C:16 N:1 P:0.001 Fe" signifying that in iron deficient conditions each atom of iron can fix 106,000 atoms of carbon, or on a mass basis, each kilogram of iron can fix 83,000 kg of $CO_2$. The 2004 EIFEX experiment reported a carbon dioxide to iron export ratio of nearly 3000 to 1. The atomic ratio would be approximately: "3000 C:58,000 N:3,600 P:1 Fe".

Food Webs

Microalgae living on ice are feeding all trophic levels of food chains including top predators like Polar Bears Researchers found that the majority of polar bears' diet is made up of critters that ultimately depend on sea-ice algae as a food source. (Liz Allen 2021) 2021/01/03/no-polar-bears-do-not-live-in-antarctica-but-could-they/

Much of the deep ocean that's now decertified thanks to human activity was once a thriving aquatic ecosystem. Our current research explores how whales form an important part of rebuilding that system, acting as "biological pumps" that circulate nutrients from the depths of the ocean to its surface through their feeding and excreting behaviors.

Storing Carbon in the Sea the Conversation: Published: Apr. 11, 2022, 3:45 pm BST Oceans are better at storing carbon than trees. In a warmer future, ocean carbon sinks could help stabilize our planet What's more, CCRC experiments are exploring the potential for regenerating ocean biomass to store more carbon. Ocean biomass refers to communities of plants, fish and mammals that thrive near the surface, but send their shells, bones and decomposing vegetation permanently to the deep ocean, locking huge amounts of carbon into the seabed. Expanding their numbers could bolster biodiversity, shore up fish stocks and provide income opportunities for marginalized communities across the world—as well as capturing tens of billions of tons of $CO_2$ from the atmosphere.

A third aspect of tackling the climate crisis involves fixing parts of the climate system that have already passed their "tipping point": starting by refreezing the Arctic. Rapid Arctic melting has already caused many of the extreme weather events we've seen recently, from snow in Texas to floods in China, thanks to its distorting effects on the polar jet stream. Reversing this process—for example by artificially increasing cloud cover over the region to reflect more sunlight away from Arctic ice—would allow the jet stream to return to normal, buying us more time to work on reducing atmospheric greenhouse gas levels.

Sequestration

Carbon is not considered "sequestered" unless it settles to the ocean floor where it may remain for millions of years. Most of the carbon that sinks beneath plankton blooms is dissolved and re-mineralized well above the seafloor and eventually (days to centuries) returns to the atmosphere, negating the original benefit. Trees and grasslands are viewed as important carbon sinks. Forest biomass sequesters carbon for decades, but carbon that sinks below the marine thermocline (100-200 meters) is removed from the atmosphere for hundreds of years or longer, whether it is re-mineralized or not. Since deep ocean currents take so long to resurface, their carbon content is effectively sequestered by the criterion in use today. phys.org/news/2017-01-carbon-climate.html new findings on carbon cycle feed climate research by Florida State University Jan. 23, 2017.

In the Proceedings of the National Academy of Sciences, FSU Assistant Professor Michael Stukel explains how carbon is transported to deeper waters and why it is happening more Algae in the surface ocean contribute half of the Earth's photosynthesis, but most of the carbon dioxide they take up gets released back to the atmosphere when they die," Stukel said. "The only way for this carbon to stay out of the atmosphere for a long period of time is to get it into the deep ocean. If it's in the deep ocean, t can stay put for hundreds to 1,000 years."

Mineral Enhancement

Both dust (Warren 1984) and snow algae (Benning et al. 2014; Kohshima et al. 1993; Lutz et al. 2014; Thomas and Duval 1995) strongly decrease the albedo of snow. Previous work has shown that minerals enhance snow algae growth in otherwise low-Fe systems (Harrold et al. 2018). Batch growth experiments with the snow algae *C. brevispina*, and the minerals andradite, forsterite, and quartz, were performed to observe differences in attachment of snow algae to such mineral surfaces. The difference in maximum counts per pixel of Fe intensities between abiotic and biotic conditions suggest biologically enhanced Fe precipitation. Number of snow algae on the surface increases with the concentration of snow algae in the medium. This result is consistent with the electrostatic attraction present between positively charged olivine and negatively charged snow algae cells at the pH (5.5) of our experiments. In contrast, the snow algae concentration present on the Fe-rich andradite remain high even when the concentration of snow algae in solution is greatly decreased. These results indicate that snow algae preferentially grow on Fe-rich surfaces. Additionally, mXRF measurements reveal that snow algae increase the formation of Fe-containing precipitates relative to abiotic controls. These results suggest that increased dust-on-snow deposition in a drying climate can lead to additional snow algal growth. Formation of Fe-containing precipitates by snow algae may further decrease snow albedo, resulting in a positive feedback loop that will likely exacerbate climate change.

Cryoconite is a deposit of dust and soot, often bound by microbial mats, that is formed on melting glaciers and ice sheets. The deposits are often found in pothole-like pockets on the ice surface. Of the cryoconite hole water chemistry along the glacier centerline shows that $Cl^-$, $Ca^{2+}$, $Na^+$; and $Mg^{2+}$ are the dominant ions and that concentrations of $Cl^-$, $Ca^{2+}$, and $Mg^{2+}$ are up to an order of magnitude higher than in clean glacier ice www.researchgate.net/

Measuring and Monitoring from Space

Andrew Gray et al, 2021 present the first estimate of green snow algae community biomass and distribution along the Antarctic Peninsula. Sentinel 2 imagery supported by two field campaigns revealed 1679 snow algae blooms, seasonally covering $1.95 \times 10^6$ $m^2$ and equating to $1.3 \times 10^3$ tonnes total dry biomass. Ecosystem range is limited to areas with average positive summer temperatures, and distribution strongly influenced by marine nutrient inputs, with 60% of blooms less than 5 km from a penguin colony.

The inventor in developing the invention registered for user permissions and collected data daily utilising Multi-sensor Analyzed Sea Ice Extent MASIE 1 KM all years extent of sea ice in SQ km. for all sea ice regions in the Northern Hemisphere (MASIE-NH) NOAA satellite. A distinctly L-shaped 40 km^2 ice floe off the coast off Iceland was chosen for monitoring over a few days from Jan. 31 to Feb. 7 2022.

Professor Andrew Shepherd, Director of the NERC Centre for Polar Observation and Modelling Principal Scientific Advisor to the ESA CryoSat mission As Co-leader of the ESA-NASA Ice Sheet Mass Balance Inter-comparison Exercise communicated directly with JNW advising about his findings and recommending how to receive more data in order to monitor specific icebergs from space using the ESA (European Space Agency) access FTP data portal.

This short but intense introduction to the capability of collecting data for monitoring sea ice from space endorses the method of monitoring and the willingness for cooperation at the highest level.

Sea Ice Modeling

According to a Sea Ice Model Calculator produced by the Inventor an inoculation of an iceberg the size of A76 at 4320 $km^2$ equates to a one season carbon capture sink of 1.1 Million Tonnes.

Inoculation of the A76 iceberg could amount, for example, to reducing 79% of Coca-Cola's total annual Worldwide GHG emission for 2020.

Icebergs could potentially be used as revenue generating sponsor sites for offset and production. Sponsorship opportunities from Individual Sectors, Corporations, Institutions, Environmental Groups and Governments shows a Global potential revenue of 2.2 trillion USD.

There appears to be large demand for a solution that this invention provides.

Sea Ice

Sea ice surrounds the polar region of the Earth covering on average up to 25 million $km^2$, an area 2.5 times the size of Canada.

Methods for Transportation and Deployment

Oil tankers and container ships are ideal vessels for transporting the inoculant and can be adapted to produce the inoculant whilst traveling to location.

Specialized Drones for spraying large areas and/or adapted crop spraying aircraft can be used for deploying the algal inoculant.

Carbon dioxide is identified as a greenhouse gas that is a major contributor to the increase in global temperature. Removing high levels of the heat absorbing carbon dioxide from the atmosphere can reduce the rise in global temperature. The present invention provides product and methods that can ingest carbon dioxide ($CO_2$) from air flowing by, over, or around the product, hereinafter RubisCO Climate Vaccine® (RCV) sequester carbon within product elements, produce (self-propagate) additional functional vaccine elements, precipitate to ground or water. Following precipitation, the vaccine, including progeny elements integrates into the algal pathways, providing a link in the food chain and more permanent deposition of the sequestered carbon as detritus/muck.

The vaccine comprises live microorganisms that post deployment converts gaseous $CO_2$ that can sequester the carbon as perhaps 20% enters the food chain with the remaining 80% being sequestered essentially permanently.

Whilst it is known that many microorganisms utilize carbon dioxide from the atmosphere to photosynthesize, the invention is unique in that it is a specifically designed and cultured cocktail of constituent ingredients and developmental stages of the microorganisms to enable optimized growth in the extreme atmospheric conditions for its deployed inoculation. The location for the dose, the amount, its developmental status for each inoculation is governed by threshold values of temperature, atmospheric pressure, humidity, diurnal light period and intensity and predicted patterns of environmental distribution that will enable optimized growth and replication efficacy over the period from its initial inoculation until its deposition. Whilst its growth and replication are a naturally occurring process the RCV is inoculated into new and previously microorganism uncolonized environments.

The preferred RCV is a cocktail of selected cultured extremophile psychrophile microorganisms specific for optimal growth and hence carbon capture in the ambient conditions. The RCV is cultured to a specific concentration density for distribution. The RCV contains inorganic trace nutrients as growth accelerants. The RCV contains inert light absorbing particles as accelerant growth nuclei. The RCV can be transported and stored in diluted or concentrated form for long periods in cool light proof containers or as a dried powder. The RCV origin cultured phials/agar slopes should be refrigerated at a temperature below 4° C. These storage conditions will minimize potential biomass degradation for mid to long term storage.

The RCV of the present invention is formed as a cocktail of selected cultured psychrophile microorganisms that are serially cultured and combined for optimal growth and hence carbon capture in the target ambient conditions, for example an ice sheet or a purpose created ice rink. As the cultured cocktail "grows" each element becomes larger and produces progeny. The progeny continues to consume $CO_2$ and to grow and proliferate compounding offspring. During the production phase, the RCV is cultured to a desired concentration density for distribution at the target site. In addition to the cultured psychrophile microorganisms, the RCV comprises inorganic trace nutrients as growth accelerants Inert light absorbing particles are included as accelerant growth nuclei. The RCV can be transported and can be stored in a diluted or as a concentrated form for long periods in cool light proof containers. In the absence of light, the cultures maintain dormancy, but are activated when dispersed and exposed to light. Optimally, the RCV is refrigerated at a temperature below 4° C. to minimize potential biomass degradation in mid to long term storage.

A process for implementing the vaccine at a desired target site, e.g., on an iceberg, an expanse of ocean/sea ice, etc., may involve providing a concentrate inoculum about 22,000 cells/ml in a typical example, to a dispenser. The dispenser may itself dilute the inoculum ~100 fold, e.g., ~8 to 12 ml/liter for spreading on the ice surface. A spread rate can typically be in a range of 1 liter over ~5 to 25 m², e.g., 1 liters over each 10 square meters. The resultant dispersion comprises approximately $1.5 \times 10^6$ to $2.5 \times 10^6$ e.g., $2 \times 10^6$ cells per 100 square meters. The precise numbers will vary with size of the microorganism, quantity of accelerants, growth rates of the deployed species at the latitude and light levels present at the targeted zone(s), etc.

The cultured cocktail for atmospheric or industrial $CO_2$ removal is dispensed as a bio sustainable microalgae cocktail to capture carbon dioxide directly from its ambient gas. Inorganic accelerants in the RCV increase the absorption of specific light wavelengths for a micro temperature increase and resultant increased growth. The carrier medium enables sustainable deployment and growth for extended time and enhanced carbon capture. Accelerant nutrients are included in the vaccine to optimize growth/reproduction. As the cultured cocktail "grows" each living element becomes larger and divides producing progeny elements. These progeny continue to consume ambient $CO_2$ and to grow and proliferate exponentially compounding offspring.

The naturally occurring wild type of the microorganism species used as source material for the vaccine, flourish and capture carbon dioxide in large amounts where they grow. This invention culturally modifies wild type organisms for optimal activity at the target site where RCV is administered as a growth optimized cocktail directly at the site in quantities for accelerated carbon capture.

The RCV is superior to other Carbon Capture alternatives yet is proposed for use in conjunction with many similarly purposed activities.

The RCV works faster than any known nature-based alternatives. In natural occurring conditions it has been shown to assimilate 65% of irradiated $^{14}C$ carbon dioxide in just three hours. It exceeds known alternatives for capturing large scale amounts of carbon dioxide directly from the atmosphere. Active constituent organisms of the vaccine have been measured as capturing 40 times more carbon than an Amazonian rain forest per square meter. The growing algae in active culture can withstand high levels of UV radiation (sunlight) as well as intense daily changes in temperature (−20° C. to +20° C.). Vaccine can be transported and stored at ambient non-refrigerated temperatures. The cultured organisms can withstand low and high levels of humidity and atmospheric pressure, including water immersion in a concentrated vaccine supply. The vaccine elements are photosynthetically active at temperatures between about 0-20° C. The bulk ice may be at a lower temperature while a micro temperature localized to the vaccine organism propagation liquid air interface approximates 0° C. or warmer.

$CO_2$ assimilation rates increase with increased levels of $CO_2$ up to at least 12 ppm levels. This far exceeds current $CO_2$ in the environment (4 ppm) so even if $CO_2$ levels massively rise, The Culture Vaccine will remain effective. As the vaccine consumes and sequesters carbon from the $CO_2$ it returns free gaseous oxygen ($O_2$) to the atmosphere from previously combined oxygen in $CO_2$ rather than alternative sequestration methods, such as carbonate depositing. The environmental vaccination is more efficient and less intrusive than other recognized nature-based solutions for climate change, e.g., re-forestation.

EXAMPLE

Specific species of psychrophile algae were initially chosen for the initial vaccine trial product. Samples of wild type Antarctic snow algae: *Chlamydomonas nivalis* (CN) and *Chloromonas pichinchae* (CP) were purchased from UTEX in Texas, US. Proof of durability was seen when the purchased products were impounded by authorities for over ten days. Viability of the cultures was maintained even after the low pressures and temperatures in the plane cargo hold and normal storage conditions during the impoundment period.

The algae were serially cultured to selectively enhance growth and proliferation and capacity to capture and store carbon over the seed culture characteristics.

Examples

Specific species of psychrophile algae were initially chosen for the initial vaccine trial product. Samples of wild type Antarctic snow algae: *Chlamydomonas nivalis* (CN) and *Chloromonas pichinchae* (CP) were purchased from UTEX in Texas, US. Proof of durability was seen when the purchased products were impounded by authorities for over ten days. Viability of the cultures was maintained even after the low pressures and temperatures in the plane cargo hold and normal storage conditions during the impoundment period.

The algae were serially cultured in 3N-BBM+V medium from a 1000 ml CCAP prepared from stock solutions:

| | |
|---|---|
| NaNO$_3$ | 25.0 g |
| CaCl$_2$•2H$_2$O | 2.5 g |
| MgSO$_4$•7H$_2$O | 7.5 g |
| K$_2$HPO$_4$•3H$_2$O | 7.5 g |
| KH$_2$PO$_4$ | 17.5 g |
| NaCl | 2.5 g | with trace elements prepared in a stock of 0.75 g EDTA in 1000 ml distilled water added in the exact following sequence:

| | |
|---|---|
| FeCl$_3$•6H$_2$O | 97.0 mg |
| MnCl$_2$•4H$_2$O | 41.0 mg |
| ZnCl$_2$ | 5.0 mg |
| CoCl$_2$•6H$_2$O | 2.0 mg |
| Na$_2$MoO$_4$•2H$_2$O | 4.0 mg |
| and two vitamin supplements: | |
| Thiaminhydrochloride (B1) | 120 mg in 100 ml distilled water-sterile filtered |
| Cyanocobalamin (B$_{12}$) | 100 mg in 100 ml distilled water then diluted: 1 ml into 99 ml distilled water-sterile filtered |

From these stocks, the 3N-BBM+V medium is made by combining culture feed and growth accelerants as in the example below:

| | |
|---|---|
| NaNO$_3$ | 30.0 ml |
| CaCl$_2$•2H$_2$O | 10.0 ml |
| MgSO$_4$•7H$_2$O | 10.0 ml |
| K$_2$HPO$_4$•3H$_2$O | 10.0 ml |
| KH$_2$PO4 | 10.0 ml |
| NaCl | 10.0 ml |
| trace elements | 6.0 ml |
| B$_1$ | 1.0 ml |
| B$_{12}$ | 1.0 ml |

CN and CP samples were then cultured on agar slopes and phial solutions to obtain desired quantities and concentrations 60,000 to $10^6$ cells/ml for viability testing.

A copending application is simultaneously filed with this application. The vaccine production application filed the same day by the same Applicant/Inventor is hereby incorporated in its entirety by reference.

Cells extracted from agar after a few weeks show distinct outer coat enclosing numerous daughter cells While the inventor used the term "we" in describing this invention, it is to be understood that the inventor conceived the claimed inventions. The inventor directed associates in practicing the processes described herein. Associates also confirmed as "second eyes" reported observations.

The invention claimed is:

1. A method for mitigating effects of CO$_2$ in the atmosphere, said method comprising: spreading an effective amount of a preparation of psychrophile algae onto an environmental ice surface, thereby mitigating effects of CO2 in the atmosphere.

2. The method of claim 1 wherein said ice surface comprises floating ocean ice or sea ice.

3. The method of claim 2 wherein said ice surface comprises an iceberg.

4. The method of claim 1 wherein said ice surface is selected from the group consisting of: a frozen pool or lake, a frozen rink, a frozen canal, a frozen river, and glacier ice.

5. The method of claim 1 wherein spreading said psychrophile algae comprises preparing said psychrophile algae through serial culture that has adapted said psychrophile algae for increased growth compared to said psychrophile algae used to seed said serial culture.

6. The method of claim 1 wherein said preparation of psychrophile algae comprises a plurality of psychrophile algae species.

7. The method of claim 1 wherein said spreading comprises delivering approximately $2\times10^4$ organisms of said psychrophile algae per square meter of said environmental ice surface.

8. The method of claim 1 wherein said spreading comprises spreading liquid droplets comprising said preparation over said environmental ice surface.

9. The method of claim 1 wherein said spreading comprises spreading dry particles comprising said preparation over said environmental ice surface.

10. The method of claim 1 wherein said spreading comprises spreading from a spreading vehicle in contact with said environmental ice surface.

11. The method of claim 1 wherein said spreading comprises spreading from a spreading vehicle traversing above said environmental ice surface.

12. The method of claim 8 wherein prior to spreading, said preparation of psychrophile algae is diluted with an aqueous liquid to lessen the concentration of said psychrophile algae.

13. The method of claim 12 wherein said dilution is between 5 and 20 fold.

14. The method of claim 13 wherein said dilution is between 8 and 12 fold.

15. The method of claim 12 wherein said preparation comprises about 20,000 to 250,000 cells/ml prior to said dilution.

16. The method of claim 2 wherein said ice surface comprises sea ice.

17. The method of claim 1 wherein said spreading results in growth of said psychrophile algae.

18. The method of claim 1 wherein said environmental ice surface is floating.

19. The method of claim 1 wherein said preparation of psychrophile algae does not include any form of species of Cyanobacteria.

* * * * *